(12) United States Patent
Caldarone

(10) Patent No.: US 9,393,025 B2
(45) Date of Patent: Jul. 19, 2016

(54) USE OF REMOTE ISCHEMIC CONDITIONING FOR TRAUMATIC INJURY

(75) Inventor: Christopher Caldarone, Toronto (CA)

(73) Assignee: The Hospital for Sick Children, Toronto (CA)

( * ) Notice: Subject to any disclaimer, the term of this patent is extended or adjusted under 35 U.S.C. 154(b) by 0 days.

(21) Appl. No.: 13/082,647

(22) Filed: Apr. 8, 2011

(65) Prior Publication Data

US 2011/0251635 A1    Oct. 13, 2011

Related U.S. Application Data

(60) Provisional application No. 61/322,070, filed on Apr. 8, 2010.

(51) Int. Cl.
*A61B 17/00* (2006.01)
*A61B 17/132* (2006.01)
*A61B 17/135* (2006.01)
*A61H 9/00* (2006.01)

(52) U.S. Cl.
CPC .......... *A61B 17/132* (2013.01); *A61B 17/1355* (2013.01); *A61H 9/0078* (2013.01)

(58) Field of Classification Search
CPC . A61B 17/132; A61B 17/1355; A61H 9/0078
USPC .......... 606/201–203, 157, 158; 600/490–492, 600/309; 128/898
See application file for complete search history.

(56) References Cited

U.S. PATENT DOCUMENTS

| | | | |
|---|---|---|---|
| 3,552,383 | A | 1/1971 | Krueger et al. |
| 4,106,002 | A | 8/1978 | Hogue, Jr. |
| 4,206,764 | A | 6/1980 | Williams |
| 4,321,929 | A | 3/1982 | Lemelson et al. |
| 4,664,651 | A | 5/1987 | Weinshenker et al. |
| 5,135,003 | A | 8/1992 | Souma |
| 5,267,565 | A | 12/1993 | Beard |
| 5,569,304 | A | 10/1996 | Ulrich |
| 5,571,075 | A | 11/1996 | Bullard |
| 5,634,467 | A | 6/1997 | Nevo |
| 5,651,369 | A | 7/1997 | Tomita |
| 6,020,334 | A | 2/2000 | Fukushi et al. |
| 6,152,881 | A | 11/2000 | Raines et al. |
| 6,210,423 | B1 | 4/2001 | Kim |
| 6,303,649 | B1 | 10/2001 | Hattori et al. |
| 6,485,429 | B2 | 11/2002 | Forstner |
| 6,550,482 | B1 | 4/2003 | Burbank et al. |

(Continued)

FOREIGN PATENT DOCUMENTS

| | | |
|---|---|---|
| AU | 2011237461 B2 | 3/2016 |
| CA | 2692463 A1 | 1/2009 |

(Continued)

OTHER PUBLICATIONS

Kharbanda et al. ,"Translation of remote ischaemic preconditioning into clinical practice," Lancet, 374: pp. 1557-1565, Oct. 31, 2009.*

(Continued)

*Primary Examiner* — Julian W Woo
(74) *Attorney, Agent, or Firm* — Wolf, Greenfield & Sacks, P.C.

(57) ABSTRACT

The invention provides methods for reducing traumatic injury through the use of ischemic conditioning.

24 Claims, 5 Drawing Sheets

(56) References Cited

U.S. PATENT DOCUMENTS

| | | |
|---|---|---|
| 6,626,840 B2 | 9/2003 | Drzewiecki et al. |
| 6,660,759 B1 | 12/2003 | Hattori et al. |
| 6,670,362 B2 | 12/2003 | Banks et al. |
| 6,702,720 B2 | 3/2004 | Dardik |
| 6,719,704 B2 | 4/2004 | Narimatsu et al. |
| 6,858,012 B2 | 2/2005 | Burns et al. |
| 6,962,599 B2 | 11/2005 | Hui |
| 7,004,907 B2 | 2/2006 | Banet et al. |
| 7,018,335 B2 | 3/2006 | Kario et al. |
| 7,048,702 B2 | 5/2006 | Hui |
| 7,314,478 B2 | 1/2008 | Hui |
| 7,338,410 B2 | 3/2008 | Dardik |
| 7,374,540 B2 | 5/2008 | Schnall |
| 7,390,303 B2 | 6/2008 | Dafni |
| 7,517,312 B2 | 4/2009 | Loeb et al. |
| 7,615,548 B2 | 11/2009 | Gottlieb et al. |
| 7,635,722 B1 | 12/2009 | Bachynsky et al. |
| 7,689,286 B2 | 3/2010 | Pastore et al. |
| 7,717,855 B2 | 5/2010 | Caldarone et al. |
| 8,753,283 B2 * | 6/2014 | Leschinsky ........ A61B 5/02208 606/201 |
| 8,764,789 B2 | 7/2014 | Ganske et al. |
| 8,790,266 B2 | 7/2014 | Caldarone et al. |
| 8,911,469 B2 * | 12/2014 | Raheman ................. 606/202 |
| 9,119,759 B2 | 9/2015 | Caldarone |
| 9,119,761 B2 | 9/2015 | Redington |
| 9,205,019 B2 | 12/2015 | Ganske et al. |
| 2001/0029389 A1 | 10/2001 | Kim |
| 2003/0013974 A1 | 1/2003 | Natarajan et al. |
| 2003/0065270 A1 | 4/2003 | Raines et al. |
| 2003/0143662 A1 | 7/2003 | Cummings et al. |
| 2003/0176795 A1 | 9/2003 | Harris et al. |
| 2003/0216651 A1 | 11/2003 | Burns et al. |
| 2003/0233118 A1 | 12/2003 | Hui |
| 2004/0044290 A1 | 3/2004 | Ward et al. |
| 2004/0064076 A1 | 4/2004 | Bilgi |
| 2004/0102818 A1 | 5/2004 | Hakky et al. |
| 2004/0134492 A1 | 7/2004 | Dardik |
| 2004/0241634 A1 | 12/2004 | Millis et al. |
| 2004/0255956 A1 * | 12/2004 | Vinten-Johansen et al. .. 128/898 |
| 2005/0004476 A1 | 1/2005 | Payvar et al. |
| 2005/0070405 A1 | 3/2005 | Egger |
| 2005/0159640 A1 | 7/2005 | Barbut et al. |
| 2005/0177078 A1 | 8/2005 | Loeb et al. |
| 2006/0024779 A1 | 2/2006 | Cummings et al. |
| 2006/0052712 A1 | 3/2006 | Poliac et al. |
| 2006/0052713 A1 | 3/2006 | Poliac et al. |
| 2006/0052714 A1 | 3/2006 | Poliac et al. |
| 2006/0058717 A1 | 3/2006 | Hui et al. |
| 2006/0100639 A1 | 5/2006 | Levin et al. |
| 2006/0142663 A1 | 6/2006 | Sawanoi et al. |
| 2007/0150005 A1 | 6/2007 | Sih et al. |
| 2008/0097385 A1 | 4/2008 | Vinten-Johansen et al. |
| 2008/0139949 A1 | 6/2008 | Caldarone et al. |
| 2008/0222769 A1 | 9/2008 | Natonson et al. |
| 2009/0137884 A1 * | 5/2009 | Naghavi et al. ............ 600/309 |
| 2009/0192128 A1 | 7/2009 | Worcel et al. |
| 2009/0221649 A1 | 9/2009 | Krahn et al. |
| 2009/0238852 A1 | 9/2009 | Kennedy et al. |
| 2009/0287069 A1 | 11/2009 | Naghavi et al. |
| 2009/0324748 A1 | 12/2009 | Dobson |
| 2010/0081941 A1 | 4/2010 | Naghavi et al. |
| 2010/0105993 A1 | 4/2010 | Naghavi et al. |
| 2010/0160444 A1 | 6/2010 | Gottlieb et al. |
| 2010/0160799 A1 | 6/2010 | Caldarone et al. |
| 2010/0185220 A1 * | 7/2010 | Naghavi et al. ............ 606/158 |
| 2010/0292619 A1 | 11/2010 | Redington et al. |
| 2010/0305607 A1 | 12/2010 | Caldarone et al. |
| 2010/0322467 A1 | 12/2010 | Reed et al. |
| 2010/0324429 A1 | 12/2010 | Leschinsky |
| 2010/0328142 A1 | 12/2010 | Zoughi et al. |
| 2011/0190807 A1 | 8/2011 | Redington et al. |
| 2011/0238107 A1 * | 9/2011 | Raheman ................. 606/202 |
| 2011/0240043 A1 | 10/2011 | Redington |
| 2012/0130419 A1 | 5/2012 | Leschinsky |
| 2012/0277789 A1 | 11/2012 | Caldarone et al. |
| 2013/0211269 A1 | 8/2013 | Leschinsky et al. |
| 2013/0317581 A1 | 11/2013 | Redington |
| 2014/0296756 A1 | 10/2014 | Ganske et al. |
| 2016/0015553 A1 | 1/2016 | Caldarone |
| 2016/0022269 A1 | 1/2016 | Ganske et al. |
| 2016/0038147 A1 | 2/2016 | Redington |
| 2016/0038737 A1 | 2/2016 | Redington |
| 2016/0045726 A1 | 2/2016 | Redington |

FOREIGN PATENT DOCUMENTS

| | | |
|---|---|---|
| CN | 2395559 | 9/2000 |
| CN | 201098315 Y | 8/2008 |
| CN | 101317805 A | 12/2008 |
| CN | 201316381 Y | 9/2009 |
| EP | 0 960 598 A1 | 12/1999 |
| EP | 1 016 379 A1 | 7/2000 |
| EP | 1 249 218 A2 | 10/2002 |
| GB | 1 323 365 A | 7/1973 |
| GB | 2 434 536 A | 8/2007 |
| JP | 2001221 A | 1/1990 |
| JP | 07-051276 | 2/1995 |
| JP | 2001505472 A | 4/2001 |
| JP | 2002539879 A | 11/2002 |
| RU | 2 253 429 C1 | 6/2005 |
| WO | WO 83/00995 A1 | 3/1983 |
| WO | WO 91/18571 A1 | 12/1991 |
| WO | WO 98/30144 A1 | 7/1998 |
| WO | WO 00/56261 A1 | 9/2000 |
| WO | WO 00/57776 A1 | 10/2000 |
| WO | WO 2004/004702 A2 | 1/2004 |
| WO | WO 2005/011503 A1 | 2/2005 |
| WO | WO 2005/077265 A1 | 8/2005 |
| WO | WO 2006/024871 A1 | 3/2006 |
| WO | WO 2006/030441 A2 | 3/2006 |
| WO | WO 2006/061825 A2 | 6/2006 |
| WO | WO 2006/069170 A2 | 6/2006 |
| WO | WO 2006/099958 A1 | 9/2006 |
| WO | WO 2007/085828 A1 | 8/2007 |
| WO | WO 2008/148045 A1 | 12/2008 |
| WO | WO 2008/148062 A1 | 12/2008 |
| WO | WO 2009/010810 A2 | 1/2009 |
| WO | WO 2011/121402 A2 | 10/2011 |
| WO | WO 2012/016280 A1 | 2/2012 |

OTHER PUBLICATIONS

Ali et al., Remote ischemic preconditioning reduces myocardial and renal injury after elective abdominal aortic aneurysm repair: a randomized controlled trial. Circulation. Sep. 11, 2007;116(11 Suppl):I98-105.

Bartekova et al., Liver ischemia induced remote preconditioning: role of cardioprotective proteins. 25. ISHR-ES meeting. Jun. 21-25, 2005. Tromsoe, Norway. J Mol Cell Cardiol. 2005;38(6):1004.

Bøtker et al., Upper-limb ischemia during ambulance transfer reduces myocardial perfusion injury in STEMI. Heartwire. Mar. 28, 2009. Featured at i2 Session of AAC. Mar. 28-31, 2009. Last Accessed on Mar. 5, 2012 from http://www.theheart.org/article/951627.do.

Bøtker et al., Remote ischaemic conditioning before hospital admission, as a complement to angioplasty, and effect on myocardial salvage in patients with acute myocardial infarction: a randomised trial. Lancet. Feb. 27, 2010;375(9716):727-34.

Brzozowski et al., Ischemic preconditioning of remote organs attenuates gastric ischemia-reperfusion injury through involvement of prostaglandins and sensory nerves. Eur J Pharmacol. Sep. 19, 2004;499(1-2):201-13.

Champion et al., A profile of combat injury. J Trauma. May 2003;54(5 Suppl):S13-9.

Cheung et al., Randomized controlled trial of the effects of remote ischemic preconditioning on children undergoing cardiac surgery: first clinical application in humans. J Am Coll Cardiol. Jun. 6, 2006;47(11):2277-82.

Dickson et al., Rabbit heart can be "preconditioned" via transfer of coronary effluent. Am J Physiol. Dec. 1999;277(6 Pt 2):H2451-7.

(56) References Cited

OTHER PUBLICATIONS

Dong et al., Limb ischemic preconditioning reduces infarct size following myocardial ischemia-reperfusion in rats] Sheng Li Xue Bao. Feb. 25, 2004;56(1):41-6. Chinese.

Gho et al., Myocardial protection by brief ischemia in noncardiac tissue. Circulation. Nov. 1, 1996;94(9):2193-200.

Hausenloy et al., Effect of remote ischaemic preconditioning on myocardial injury in patients undergoing coronary artery bypass graft surgery: a randomised controlled trial. Lancet. Aug. 2007.

Hausenloy et al., Preconditioning and postconditioning: underlying mechanisms and clinical application. Atherosclerosis. Jun. 2009;204(2):334-41. Epub Nov. 5, 2008.

Hausenloy et al., The therapeutic potential of ischemic conditioning: an update. Nat Rev Cardiol. Jun. 21, 2011;8(11):619-29.

Holcomb et al., Understanding combat casualty care statistics. J Trauma. Feb. 2006;60(2):397-401.

Hoole et al., Cardiac Remote Ischemic Preconditioning in Coronary Stenting (CRISP Stent) Study: a prospective, randomized control trial. Circulation. Feb. 17, 2009;119(6):820-7. Epub Feb. 2, 2009.

Jan et al., Limb ischemic preconditioning mitigates lung injury induced by haemorrhagic shock/resuscitation in rats. Resuscitation. Jun. 2011;82(6):760-6. Epub Mar. 12, 2011.

Jenkins et al., Ischaemic preconditioning reduces troponin T release in patients undergoing coronary artery bypass surgery. Heart. Apr. 1997;77(4):314-8.

Kharbanda et al., Ischemic preconditioning prevents endothelial injury and systemic neutrophil activation during ischemia-reperfusion in humans in vivo. Circulation. Mar. 27, 2001;103(12):1624-30.

Kharbanda et al., Remote ischaemic preconditioning protects against cardiopulmonary bypass-induced tissue injury: a preclinical study. Heart. Oct. 2006;92(10):1506-11. Epub Jul. 3, 2006.

Kharbanda et al., Transient limb ischemia induces remote ischemic preconditioning in vivo. Circulation. Dec 3, 2002;106(23):2881-3.

Konstantinov et al., Remote ischemic preconditioning of the recipient reduces myocardial ischemia-reperfusion injury of the denervated donor heart via a Katp channel-dependent mechanism. Transplantation. Jun. 27, 2005;79(12):1691-5.

Konstantinov et al., The remote ischemic preconditioning stimulus modifies inflammatory gene expression in humans. Physiol Genomics. 2004 Sep 16;19(1):143-50. Epub Aug. 10, 2004.

Konstantinov et al., The remote ischemic preconditioning stimulus modifies gene expression in mouse myocardium. J Thorac Cardiovasc Surg. Nov. 2005;130(5):1326-32.

Lang et al., Myocardial preconditioning and remote renal preconditioning—identifying a protective factor using proteomic methods? Basic Res Cardiol. Mar. 2006;101(2):149-58. Epub Nov. 11, 2005.

Laskey et al., Frequency and clinical significance of ischemic preconditioning during percutaneous coronary intervention. J Am Coll Cardiol. Sep. 17, 2003;42(6):998-1003.

Leesar et al., Nonelectrocardiographic evidence that both ischemic preconditioning and adenosine preconditioning exist in humans. J Am Coll Cardiol. Aug. 6, 2003 ;42(3):437-45.

Leesar et al., Preconditioning of human myocardium with adenosine during coronary angioplasty. Circulation. Jun. 3, 1997;95(11):2500-7.

Loukogeorgakis et al., Remote ischemic preconditioning provides early and late protection against endothelial ischemia-reperfusion injury in humans: role of the autonomic nervous system. J Am Coll Cardiol. Aug. 2, 2005;46(3):450-6.

McCully et al., Adenosine-enhanced ischemic preconditioning: adenosine receptor involvement during ischemia and reperfusion. Am J Physiol Heart Circ Physiol. Feb. 2001;280(2):H591-602.

Murry et al., Preconditioning with ischemia: a delay of lethal cell injury in ischemic myocardium. Circulation. Nov. 1986;74(5):1124-36.

Nandagopal et al., Critical role for nitric oxide signaling in cardiac and neuronal ischemic preconditioning and tolerance. J Pharmacol Exp Ther. May 2001;297(2):474-8.

Peng et al., The protective effects of ischemic and calcitonin gene-related peptide-induced preconditioning on myocardial injury by endothelin-1 in the isolated perfused rat heart. Life Sci. 1996;59(18):1507-14.

Penttila et al., Ischemic preconditioning does not improve myocardial preservation during off-pump multivessel coronary operation. Ann Thorac Surg. Apr. 2003;75(4):1246-52; discussion 1252-3.

Peralta et al., Liver ischemic preconditioning: a new strategy for the prevention of ischemia-reperfusion injury. Transplant Proc. Aug. 2003;35(5):1800-2.

Przyklenk et al., Regional ischemic 'preconditioning' protects remote virgin myocardium from subsequent sustained coronary occlusion. Circulation. Mar. 1993;87(3):893-9.

Schmidt et al., Intermittent peripheral tissue ischemia during coronary ischemia reduces myocardial infarction through a Katp-dependent mechanism: first demonstration of remote ischemic perconditioning. Am J Physiol Heart Circ Physiol. Apr. 2007;292(4):H1883-90. Epub Dec. 15, 2006.

Schoemaker et al., Bradykinin mediates cardiac preconditioning at a distance. Am J Physiol Heart Circ Physiol. May 2000;278(5):H1571-6.

Tomai et al., Ischemic preconditioning in humans: models, mediators, and clinical relevance. Circulation. Aug. 3, 1999;100(5):559-63.

Wolfrum et al., Calcitonin gene related peptide mediates cardioprotection by remote preconditioning. Regul Pept. Apr. 15, 2005;127(1-3):217-24.

Loukogeorgakis et al., Transient limb ischemia induces remote preconditioning and remote postconditioning in humans by a K(ATP)-channel dependent mechanism. Circulation. Sep 18, 2007;116(12):1386-95. Epub Aug 27, 2007.

Saxena et al., Remote ischemic conditioning: evolution of the concept, mechanisms, and clinical application. J Card Surg. Jan.-Feb. 2010;25(1):127-34. Epub Jun. 22, 2009 .

International Preliminary Report on Patentability for PCT/US2011/031674 mailed Oct. 18, 2012.

Addison et al., Noninvasive remote ischemic preconditioning for global protection of skeletal muscle against infarction. Am J Physiol Heart Circ Physiol. 2003;285:H1435-1443.

Ali et al., Induced remote ischemic pre-conditioning on ischemia-reperfusion injury in patients undergoing coronary artery bypass. J Coll Physicians Surg Pak. Jul. 2010;20(7):427-431.

Bauer et al., Does preconditioning protect the coronary vasculature from subsequent ischemia/reperfusion injury? Circulation. Aug. 1993;88(2):659-72.

Choi et al., Effect of remote ischemic preconditioning on renal dysfunction after complex valvular heart surgery: A randomized controlled trial. J Thorac Cardiovasc Surg. 2011;142:148-154.

D'Ascenzo et al., Remote ischaemic preconditioning in coronary artery bypass surgery: a meta-analysis. Heart. Sep. 2012;98(17):1267-71.

Dave et al., Remote organ ischemic preconditioning protect brain from ischemic damage following asphyxial cardiac arrest. Neurosci Lett. Aug. 14, 2006;404(1-2):170-5. Epub Jun. 15, 2006 .

Gurusamy et al., Ischaemic preconditioning for liver transplantation. Cochrane Database Syst Rev. 2008:CD006315.

Hahn et al., Remote ischemic pre-conditioning: A novel therapy for acute stroke? Stroke. Aug. 2011;42:2960-2962.

Harkin et al., Ischemic preconditioning before lower limb ischemia—reperfusion protects against acute lung injury. J Vasc Surg. Jun. 2002;35(6):1264-73.

Jensen et al., Remote ischemic preconditioning protects the brain against injury after hypothermic circulatory arrest. Circulation. Feb. 22, 2011;123(7):714-721. Epub Feb. 7, 2011.

Kanoria et al., Remote ischaemic preconditioning of the hind limb reduces experimental liver warm ischaemia-reperfusion injury. Br J Surg. Jun. 2006;93(6):762-8.

Karuppasamy et al., Remote intermittent ischemia before coronary artery bypass graft surgery: a strategy to reduce injury and inflammation? Basic Res Cardiol. Jun. 2011;106(4):511-9. Epub May 5, 2011.

Kharbanda et al., Translation of remote ischaemic preconditioning into clinical practice. Lancet. Oct. 31, 2009;374(9700):1557-65.

(56) References Cited

OTHER PUBLICATIONS

Koch et al., . Remote ischemic limb preconditioning after subarachnoid hemorrhage: a phase Ib study of safety and feasibility. Stroke. May 2011;42(5):1387-91. Epub Mar. 17, 2011.
Lazaris et al., Protective effect of remote ischemic preconditioning in renal ischemia/reperfiision injury, in a model of thoracoabdominal aorta approach. J. Surg Res. 2009;154:267-273.
Rahman et al., Remote ischemic preconditioning in human coronary artery bypass surgery: from promise to disappointment? Circulation. 2010;122:S53-59.
Ren et al., Limb remote-preconditioning protects against focal ischemia in rats and contradicts the dogma of therapeutic time windows for preconditioning. Neuroscience. Feb. 19, 2008;151(4):1099-103. Epub Dec. 15, 2007.
Rentoukas et al., Cardioprotective role of remote ischemic periconditioning in primary percutaneous coronary intervention: enhancement by opioid action. JACC Cardiovasc Interv. Jan. 2010;(3)(1):49-55.
Shimizu et al., Effects of intermittent lower limb ischaemia on coronary blood flow and coronary resistance in pigs. Acta Physiol (Oxf). Jun. 2007;190(2):103-9. Epub Mar. 30, 2007.
Shimizu et al., Remote ischemic preconditioning decreases adhesion and selectively modifies functional responses of human neutrophils. J Surg Res. Jan. 2010;158(1):155-61.
Shimizu et al., Transient limb ischaemia remotely preconditions through a humoral mechanism acting directly on the myocardium: evidence suggesting cross-species protection. Clin Sci (Lond). Aug. 3, 2009;117(5):191-200.
Steensrud et al., Pretreatment with the nitric oxide donor SNAP or nerve transection blocks humoral preconditioning by remote limb ischemia or intra-arterial adenosine. Am J Physiol Heart Circ Physiol. Nov. 2010;299(5):H1598-603. doi: 10.1152/ajpheart.00396.2010. Epub Aug. 27, 2010.
Venugopal et al., Effect of remote ischemic preconditioning on acute kidney injury in nondiabetic patients undergoing coronary artery bypass graft surgery: a secondary analysis of 2 small randomized trials. Am J Kidney Dis. Dec. 2010; 5(6): 1043-9.
Walsh et al., Remote ischemic preconditioning for renal and cardiac protection during endovascular aneurysm repair: a randomized controlled trial. J Endovasc Ther. Dec. 2009;16(6):680-9.
Xin et al., Combined local ischemic postconditioning and remote perconditioning recapitulate cardioprotective effects of local ischemic preconditioning. Am J Physiol Heart Circ Physiol. Jun. 2010;298(6):H1819-31. Epub Mar. 5, 2010. Erratum in: Am J PhysiolHeart Circ Physiol. Sep. 2010;299(3):H957.
Zhou et al., Limb ischemic preconditioning reduces heart and lung injury after an open heart operation in infants. Pediatr Cardiol. Jan. 2010;31(1):22-9. Epub Sep. 29, 2009.
Zimmerman et al., Ischemic preconditioning at a remote site prevents acute kidney injury in patients following cardiac surgery. Kidney Int. 2011;80:861-867.
Kin et al., Postconditioning attenuates myocardial ischemia-reperfusion injury by inhibiting events in the early minutes of reperfusion. Cardiovasc Res. Apr. 1, 2004;62(1):74-85.
Liu et al., Remote ischemic postconditioning promotes the survival of retinal ganglion cells after optic nerve injury. J Mol Neurosci. Nov. 2013;51(3):639-46. doi: 10.1007/s12031-013-0036-2. Epub Jun. 5, 2013.
Meng et al., Upper limb ischemic preconditioning prevents recurrent stroke in intracranial arterial stenosis. Neurology. Oct. 30, 2012;79(18):1853-1861. Epub Oct. 3, 2012.
Slepian et al., Pre-conditioning of smooth muscle cells via induction of the heat shock response limits proliferation following mechanical injury. Biochem Biophys Res Commun. Aug. 14, 1996;225(2):600-7.
Tanaka et al., Expression of heat shock protein after ischemic preconditioning in rabbit hearts Jpn Circ J. Jul. 1998;62(7):512-6.
Wang et al., Remote Ischemic Preconditioning Protects against Liver Ischemia-Reperfusion Injury via Heme Oxygenase-1-Induced Autophagy. PLoS One. Jun. 10, 2014;9(6):e98834. doi 10.1371/journal.pone.0098834. eCollection 2014. 12 pages.
Australian Second Examination Report for Application No. AU2011237461 issued Apr. 14, 2015.
Andreka et al., Remote ischaemic postconditioning protects the heart during acute myocardial infarction in pigs. Heart. Jun. 2007;93(6):749-52. Epub Apr. 20, 2007.
Leconte et al., Delayed hypoxic postconditioning protects against cerebral ischemia in the mouse. Stroke. Oct. 2009;40(10):3349-55. doi: 10.1161/STROKEAHA.109.557314. Epub Jul. 23, 2009.
Ludman et al., Cardiac preconditioning for ischaemia: lost in translation. Dis Model Mech, Jan.-Feb. 2010;3(1-2):35-8. doi: 10.1242/dmm.003855.
Ren et al., Limb remote ischemic postconditioning protects against focal ischemia in rats. Brain Res. Sep. 8, 2009;1288:88-94. doi: 10.1016/j.brainres.2009.07.029. Epub Jul. 23, 2009.
Toledo-Pereyra et al., Molecular signaling pathways in ischemia/reperfusion. Exp Clin Transplant. Jun. 2004;2(1):174-7.
Wang et al., Remote ischemic preconditioning by hindlimb occlusion prevents liver ischemic/reperfusion injury: the role of High Mobility Group-Box 1. Ann Surg. Feb. 2010;251(2):292-9. doi: 10.1097/SLA.0b013e3181bfda8c. Abstract.
Warzecha et al., Ischaemic preconditioning of the hundlimb or kidney does not attenuate the severity of acute ischemia/reperfusion-induced pancreaitis in rats. J Physiol Pharmacol. Jun. 2008;59(2):337-52.
Yellon et al., Preconditioning the myocardium: from cellular physiology to clinical cardiology. Physiol Rev. Oct. 2003;83(4):1113-51.
Zhao, Ischemic postconditioning as a novel avenue to protect against brain injury after stroke. J Cereb Blood Flow Metab. May 2009;29(5):873-85. doi: 10.1038/jcbfin.2009.13. Epub Feb. 25, 2009.
Australian Patent Examination Report No. 4 for Application No. AU2011237461 issued Oct. 21, 2015.
Kragh et al., "Practical Use of Emergency Tourniquets To Stop Bleeding In Major Limb Trauma," J Trauma 2008;64: S38-S50.
Australian Third Examination Report for Application No. AU2011237461 issued Sep. 29, 2015.
Jennings, "A Critical Appraisal Of The Revised Trauma Score," Australasian Journal of Paramedicine, vol. 2, Issue 1, (2004).
Babak et al., Ischemic Preconditioning As a Possible Factor for Prevention of Restenosis After Coronary Intervention. Sverdlovsk Regional Center of M.V. Savichevsky. Ekaterinburg, Russian Federation. Cardiovascular diseases: scientific conference abstracts of the IXth Russian national congress of cardiovascular surgeons. Moscow. Nov. 2003: Bulletin of the Bakoulev Center for Cardiovascular Surgery of the RAMS—2003.— vol. 4, No. 11: 18-21. Russian.
Hausenloy et al., Remote ischaemic preconditioning: underlying mechanisms and clinical application. Cardiovasc Res. 2008 Aug 1;79(3):377-86. doi: 10.1093/cvr/cvn114. Epub May 2, 2008.
Iliodromitis et al., Intravenous atenolol and esmolol maintain the protective effect of ischemic preconditioning in vivo. Eur J Pharmacol. Sep 19, 2004;499(1-2):163-9.
Li et al., Late phase of myocardial ischemic preconditioning. Adv Cardiovasc Dis. Oct 31, 2005;26(5):526-29. Chinese.
Miki et al., Captopril potentiates the myocardial infarct size-limiting effect of ischemic preconditioning through bradykinin B2 receptor activation. J Am Coll Cardiol. Nov. 15, 1996;28(6):1616-22.
Noda et al., Evidence for the delayed effect in human ischemic preconditioning. J Amer College Cardiol. 1999;34.7:1966-74.
Oxenham et al., Angiotensin-converting enzyme inhibitor treatment after myocardial infarction. A selective approach for maximum benefit. J Am Coll Cardiol. Dec. 2000;36(7):2054-5.
Spargias et al., beta blocker treatment and other prognostic variables in patients with clinical evidence of heart failure after acute myocardial infarction: evidence from the Aire study. Heart. Jan. 1999;81(1):25-32.
Tan et al., Late phase of remote ischemic preconditioning. Chongqing Medicine. Aug. 31, 2007;36(16):1608 and 1610. Chinese.

\* cited by examiner

USE OF REMOTE ISCHEMIC CONDITIONING FOR TRAUMATIC INJURY

RELATED APPLICATIONS

This application claims the benefit of U.S. Provisional Application Ser. No. 61/322,070, filed on Apr. 8, 2010, entitled "USE OF REMOTE ISCHEMIC CONDITIONING FOR TRAUMATIC INJURY", the entire contents of which are incorporated by reference herein.

BACKGROUND OF THE INVENTION

Traumatic injury is one of the leading causes of death in children and young adults. In addition, it represents a significant proportion of health care expenditures. Trauma generally refers to severe bodily injury or wounding, typically resulting from blunt force as can occur with falls, automobile accidents, domestic or industrial accidents, and in battle. Traumatic injuries should be treated immediately in order to prevent or lessen the effects of such injuries. Many of the interventions and/or therapies known to be useful at least in the acute stages of traumatic injury however are not always available.

SUMMARY OF THE INVENTION

The invention is premised, in part, on the surprising finding that deliberately performing one or more cycles of transient blood flow occlusion followed by reperfusion in a region of the body of a subject, that is remote from the region where trauma occurs or that is being protected from the effects of the trauma, reduces the effects of such trauma. The trauma may be direct trauma or indirect trauma. The trauma may or may not be associated with hypovolemia. The methods of the invention provide benefit even if resuscitation therapy is performed, and more surprisingly even if resuscitation therapy is delayed.

The invention therefore provides for the use of remote ischemic conditioning (RIC) to treat traumatic injury. The invention contemplates the use of RIC on a subject that has experienced, is experiencing, or is likely to experience trauma. In subjects that have experienced or are experiencing trauma, the invention calls for RIC during or after the trauma, or during and after the trauma. In subjects that are likely to experience trauma, the invention calls for RIC before the expected trauma and optionally during and/or after such trauma occurs.

Accordingly, in one aspect, the invention provides a method for reducing or preventing injury to cells, tissues, or organs of a body as a result of trauma comprising performing one or more cycles of blood flow occlusion followed by reperfusion on a subject before, during, and/or following trauma, wherein the blood flow occlusion and reperfusion occurs at a remote region of the body, including but not limited to one or more lower and/or upper limbs. It will be understood that the blood flow occlusion and reperfusion cycles will be performed in an amount and frequency to reduce or prevent injury. In another aspect, the invention provides a method for reducing or preventing injury to cells, tissues, or organs of a body as a result of trauma comprising performing individual or repeated RIC regimens on a subject before, during, and/or following trauma. It will be understood that the RIC regimens will be performed in an amount and a frequency sufficient to reduce or prevent injury.

In some embodiments, the injury affects multiple organs, and may be referred to as multi-organ injury or dysfunction. In some embodiments, the injury is to the lungs and/or to the liver. In some embodiments, the injury is neurological injury or dysfunction.

In another aspect, the invention provides a method for treating a subject experiencing trauma comprising performing one or more cycles of blood flow occlusion followed by reperfusion on the subject during and/or following trauma, wherein the blood flow occlusion and reperfusion occurs at a remote region of the body, including but not limited to one or more lower and/or upper limbs. In another aspect, the invention provides a method for treating a subject experiencing trauma comprising performing individual or repeated RIC regimens on the subject during and/or following trauma.

In another aspect, the invention provides a method comprising performing one or more cycles of blood flow occlusion followed by reperfusion on a subject experiencing or likely to experience trauma, wherein the one or more cycles are performed before, during and/or following trauma, wherein the blood flow occlusion and reperfusion occurs at a remote region of the body, including but not limited to one or more lower and/or upper limbs. In another aspect, the invention provides a method comprising performing individual or repeated RIC regimens on the subject experiencing or likely to experience trauma, wherein the one or more RIC regimens are performed before, during and/or following trauma.

The invention contemplates that the subject will undergo one or more than one RIC regimen. Such multiple regimens may be performed on a single day and/or over the course of several days.

In some embodiments, the trauma is hemorrhagic shock. In some embodiments, the subject may be hypotensive and/or hypovolemic. In some embodiments, the subject has lost 10%, 15%, 20%, 25%, 30%, or more of total whole blood volume. In some embodiments, the subject has received resuscitation therapy. In some embodiments, the subject has not received resuscitation therapy.

In some embodiments, the trauma is not associated with hypovolemia (e.g., the trauma may be blast injury).

In some embodiments, the repeated RIC regimens comprise more than one RIC regimen performed on a single day. In some embodiments, the repeated RIC regimens comprise two, three, four or five RIC regimens performed on a single day. In some embodiments, the repeated RIC regimens comprise one or more RIC regimens on more than one day.

In some embodiments, at least one RIC regimen is performed within 30 minutes or 1 hour of the trauma. In some embodiments, at least one RIC regimen is performed immediately after trauma.

In some embodiments, the repeated RIC regimens comprise one or more RIC regimens performed on a daily basis for one month.

In some embodiments, the RIC regimens are performed before the trauma, in which case they may be regarded as remote ischemic preconditioning regimens. In some embodiments, the RIC regimens are performed before and after the trauma. In some embodiments, the RIC regimens are performed before, during and after the trauma. In some embodiments, the RIC regimens are performed during and after the trauma. In some embodiments, the RIC regimens are performed after the trauma.

In some embodiments, the subject is human.

In some embodiments of the foregoing aspects, a single RIC cycle is performed on the subject (i.e., the subject is subjected to a period of blood flow occlusion followed by a period of reperfusion). In some embodiments, the cycle comprises about 10 minutes of blood flow occlusion and about or less than 10 minutes of reperfusion.

In some embodiments, at least one individual RIC regimen (for example, within the repeated RIC regimen) comprises at least two, at least three, or at least four cycles, each cycle comprising blood flow occlusion and reperfusion. In some embodiments, at least one RIC regimen comprises at least four cycles, each cycle comprising blood flow occlusion and reperfusion. In some embodiments, at least one RIC regimen comprises one or more cycles of about 5 minutes of blood flow occlusion and about 5 minutes of reperfusion. In some embodiments, at least one RIC regimen comprises one or more cycles of about 10 minutes of blood flow occlusion and about 10 minutes of reperfusion.

In some embodiments, blood flow occlusion is effected by applying to the remote region of the body a pressure that is above systolic pressure. In some embodiments, blood flow occlusion is effected by applying to the remote region of the body a pressure that is below systolic pressure.

In some embodiments, at least one individual RIC regimen (for example, within the repeated RIC regimen) comprises at least two, at least three, or at least four cycles, each cycle comprising supra-systolic pressure and reperfusion. In some embodiments, at least one RIC regimen comprises at least four cycles, each cycle comprising supra-systolic pressure and reperfusion. In some embodiments, at least one RIC regimen comprises one or more cycles of 5 minutes of supra-systolic pressure and 5 minutes of reperfusion. In some embodiments, the supra-systolic pressure is a pressure that is 1-5 mmHg, or 1-10 mmHg, or 1-15 mmHg above systolic pressure. In some embodiments, the supra-systolic pressure is a pressure that is at least 15 mmHg above systolic pressure. In some embodiments, the supra-systolic pressure is pressure that is about 200 mmHg.

In some embodiments, at least one individual RIC regimen (for example, within the repeated RIC regimen) comprises at least two, at least three, or at least four cycles, each cycle comprising below-systolic pressure and reperfusion.

In some embodiments, individual or repeated RIC regimens are performed at the same site. In one embodiment, individual or repeated RIC regimens are performed on an upper limb. In one embodiment, the individual or repeated RIC regimens are performed on a lower limb. In one embodiment, individual or repeated RIC regimens are performed using two or more devices such as two or more cuffs, positioned at different sites on the body (e.g., one cuff per upper limb (or arm), two cuffs on a single upper limb, one cuff per lower limb (or leg), two cuffs on a single lower limb, one cuff on an upper limb and one cuff on a lower limb, etc.).

In various embodiments, the subject may be administered two or more of these aforementioned agents.

These and other aspects and embodiments of the invention will be discussed in greater detail herein.

BRIEF DESCRIPTION OF THE FIGURES

The accompanying figures are not intended to be drawn to scale. In the figures, each identical or nearly identical component that is illustrated in various figures is represented by a like numeral. For purposes of clarity, not every component may be labeled in every figure.

Various embodiments of the invention will now be described, by way of example, with reference to the accompanying figures, in which.

DETAILED DESCRIPTION OF THE INVENTION

Figure 1:
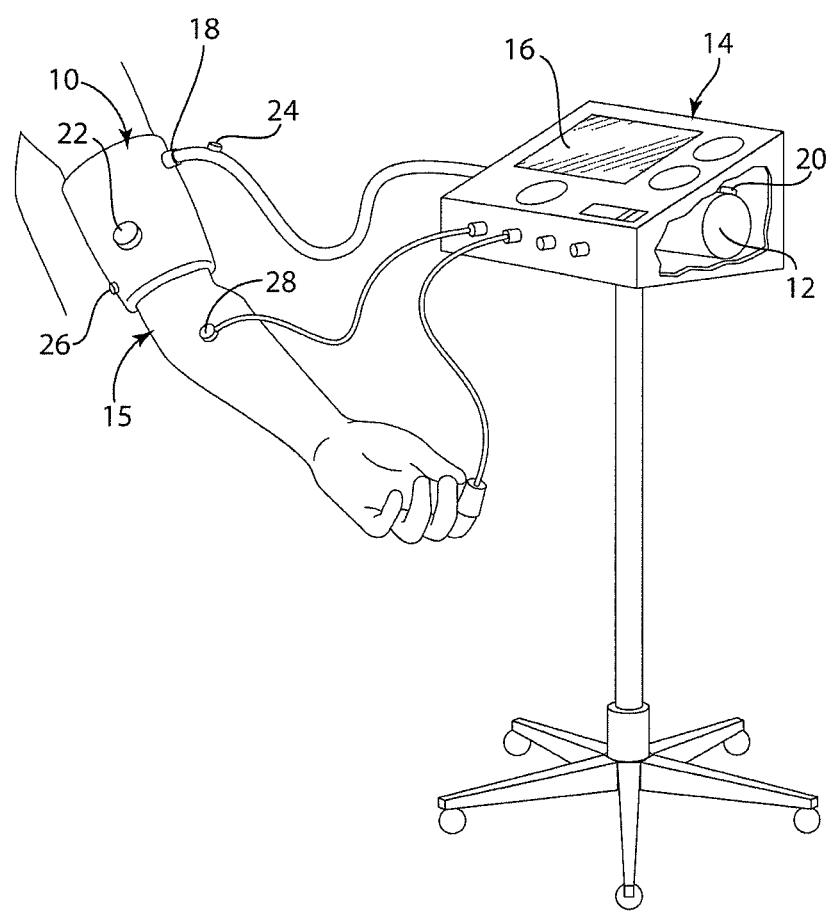
FIG. 1 is a schematic representation of one embodiment of a remote ischemic conditioning system, including a pneumatically inflatable cuff configured to contract about the limb of a subject.

The invention provides, in part, methods for treating subjects that have experienced trauma by performing on such subjects one or more RIC regimens during and/or after the trauma. The invention also provides, in part, methods for reducing the effects of trauma in subjects likely to experience trauma by performing one or more RIC regimens prior to trauma. Although not intending to be bound by any mechanism or theory of action, it is contemplated that the one or more RIC cycles or regimens reduce the degree of injury in cells, one or more tissues and/or one or more organs that would be impacted by the trauma. RIC regimens are able to ameliorate the effects of ischemia and reperfusion injury when performed before or during the time of ischemia or reperfusion. RIC is associated with suppression of immune mediators believed to be responsible for trauma-associated morbidity.

The invention relates to the performance of RIC to treat (including to ameliorate) the systemic effects associated with traumatic injury. Examples of traumatic injury that can be treated according to the invention include but are not limited to blunt trauma and hemorrhage (e.g., hemorrhagic shock). In some aspects of the invention, a subject that has sustained a traumatic injury will undergo one or more cycles of deliberately induced blood flow occlusion and reperfusion at a location on the body that is uninjured (e.g., an uninjured limb). In some aspects of the invention, a subject that has sustained a traumatic injury will undergo one or more cycles of deliberately induced ischemia and reperfusion at a location on the body that is uninjured (e.g., an uninjured limb). As described in greater detail below, these cycles constitute a regimen. A regimen may comprise 1, 2, 3, 4, 5 or more cycles. Each cycle comprises induced occlusion or ischemia for a first period of time followed by reperfusion for a second period of time. The first and second periods of time may be identical or they may be different from each other. As a non-limiting example, one or more cycles of a regimen may comprise about 5 minutes of occlusion or ischemia followed by about 5 minutes of reperfusion. As another non-limiting example, one or more cycles may comprise about 10 minutes of occlusion or ischemia followed by about 10 minutes of reperfusion. If only a single cycle is used, then the reperfusion period may be shorter than the occlusion or ischemic period (e.g., it may be less than about 1 minute, less than about 30 seconds, less than about 10 seconds, etc.).

The invention contemplates that RIC will be performed on the subject by a first responder (i.e., the first qualified person to attend to the subject). RIC can therefore be performed using an automated device (such as a pressure cuff) or manually (using a tourniquet). The ability to achieve therapeutic benefit using RIC alone is invaluable in circumstances where other interventions, including intravenous fluid resuscitation, are not available or are delayed. These circumstances include without limitation battlefield conditions during military conflicts. Accordingly, the invention contemplates that RIC can be used to reduce and/or prevent injury that is induced by trauma (e.g., hemorrhagic shock) in situations in which resuscitation therapy has not been performed or was delayed. RIC may be performed before the trauma, before resuscitation therapy, and/or after the resuscitation therapy. The invention provides intervention in the form of a light-weight, preferably automated, ischemic conditioning device that can be performed by any personnel with minimal training and minimal time required for treatment. In like manner, the invention also contemplates performing RIC on a subject in preparation for a probable traumatic injury, including for example prior to military engagement or confrontation.

Accordingly, the degree and/or severity of traumatic injury can be reduced by deliberately and repeatedly performing cycles of induced transient ischemia and reperfusion (i.e., an RIC regimen) in subjects. These subjects include those that are experiencing trauma and those that are likely to experience trauma. The ease of use of these methods make them amenable to particular circumstances including but not limited to battlefield injuries. The ability to provide therapy to such subjects, particularly where there is no other therapy or intervention immediately available, is valuable. In like manner, these methods can be used in other emergency situations in which no other therapy or intervention is immediately available such as can occur following catastrophic events such as earthquakes and other natural disasters, bombings, and the like.

The invention contemplates, in some aspects, performing a repeated RIC regimen on a subject. As used herein, an RIC regimen (or an individual RIC regimen) means at least one cycle of an induced transient ischemic event followed by a reperfusion event. An individual RIC regimen therefore may be comprised of 1, 2, 3, 4, 5, or more such cycles.

Also as used herein, a repeated RIC regimen is two or more individual RIC regimens that occur on a single day and/or one or more RIC regimens that occur on a number of days. For example, the repeated RIC regimen may comprise performing multiple RIC regimens on a single day, or performing single RIC regimens on a number of days, or performing multiple RIC regimens on a number of days. If the repeated RIC regimen occurs on a single day, the time between individual regimens may be at least 10 minutes, at least 20 minutes, at least 40 minutes, at least 1 hour, at least 2 hours, or at least 6 hours, for example. The invention contemplates that more than one RIC regimen may be performed prior to an expected trauma (such as a battlefield injury) in a short period of time in order to prepare the subject for the trauma.

As should be clear, there is no requirement that any or all of the RIC regimens in a repeated RIC regimen be identical with respect to timing, number of cycles per regimen, supra-systolic pressure, location, and the like. Moreover, even within a regimen, the times of ischemia and reperfusion may differ between cycles. Typically, however, for ease of use, the cycles within a given regimen are identical. The invention further contemplates that regimens performed prior to traumatic injury may comprise more cycles and potentially may be more frequent and/or greater in number than regimens performed during or following traumatic injury.

In some instances, RIC may be performed in an area of the body that is remote to the area of traumatic injury. However, in some instances, the effects of the traumatic injury are systemic (e.g., multi-organ injury or dysfunction) and thus RIC is performed in an area of the body that is accessible and preferably has not open wounds. Preferably but not exclusively, the RIC regimen is non-invasive. Accordingly, RIC may be performed on a limb such as an upper or lower limb. The repeated RIC regimen may be performed on a single site or on multiple sites in the body. For example, the repeated RIC regimen may comprise a first RIC regimen performed on the right upper arm, followed by a second RIC regimen performed on the left upper arm. The repeated RIC regimen may alternate between or cycle through sites on the body. In some instances, an RIC regimen may be performed on a subject at two different sites at overlapping times including simultaneously. In such instances, two devices may be used. These devices may be in communication with each other or they may be functioning independently of each other.

The subjects of the invention will preferably be humans, although non-human subjects such as companion animals (e.g., dogs, cats, etc.), agricultural or prize-winning animals (e.g., race horses, etc.) are also contemplated. Essentially, any subject that can experience traumatic injury can be treated according to the invention.

Trauma, as used herein, refers to critical or severe bodily injury, wound or shock. These forms of trauma typically require some form of resuscitation therapy. Resuscitation therapy typically involves replenishment of bodily fluids including but not limited to blood transfusion or other saline transfusion. Shock broadly refers to circulatory dysfunction. Shock may be hemorrhagic or hypovolemic shock (associated with inadequate blood volume) or it may be cardiogenic shock (associated with inadequate output of blood from the heart). Trauma associated with blood loss therefore typically also involves shock. Symptoms associated with shock include without limitation low blood pressure (i.e., hypotension), hypovolemia, hyperventilation, and cyanotic skin. In some instances, the trauma involves traumatic brain injury (e.g., the injury is to the head). In some instances, the trauma does not involve traumatic brain injury (e.g., the injury may be to the torso or one or more limbs).

Therefore, RIC may be performed on a subject that is hypovolemic and/or hypotensive. A subject that is hypovolemic may be a subject that has lost 5%, 10%, 15%, 20%, 25%, 30% or more of its whole blood volume. The cause of blood loss volume may be external bleeding, internal bleeding, or reduced blood volume resulting from excessive loss of other body fluids as may occur with diarrhea, vomiting and burns.

Trauma may result from direct injury such as penetrating injury (e.g., bullet wound). Trauma may also result from indirect injury such as, for example, a blast injury that occurs from exposure to a pressure wave following, for example, an explosion. Such latter types of trauma may occur in the absence of hypovolemia. In some instances, the invention contemplates the use of RIC after traumatic injury not associated with hypovolemia. In these and other instances, RIC may diminish systemic manifestations of the response to injury which includes neurologic injury and multi-organ dysfunction.

Since it is important to treat the subject as soon as possible, the invention contemplates that the methods provided herein may be performed in a hospital setting or in a non-hospital setting including in the environment in which the trauma occurred. RIC may be performed before the trauma occurs, and/or after the trauma occurs, including before and/or after resuscitation therapy is performed.

The repeated RIC regimens may be performed before, during and/or after trauma. In some embodiments, at least one of the RIC regimens are performed before trauma. These are referred to as remote ischemic preconditioning regimens. In these embodiments, at least one RIC regimen may be performed within about 48 hours, within about 24 hours, within about 12 hours, within about 6 hours, within about 4 hours, within about 2 hours, or within about 1 hour prior to trauma.

In some embodiments, at least one of the RIC regimens is performed after trauma has occurred. As an example, the subject may no longer by hypotensive or hypovolemic, but RIC may still be performed. These are referred to as remote ischemic post-conditioning regimens. In these embodiments, at least one RIC regimen may be performed within about 48 hours, within about 24 hours, within about 12 hours, within about 6 hours, within about 4 hours, within about 2 hours, within about 1 hour, within about 30 minutes, within about 20 minutes, within about 10 minutes, within about 5 minutes, or just immediately after the occurrence of trauma, or after the subject has been stabilized (e.g., the subject is no longer hypovolemic and/or hypotensive).

In some embodiments, the repeated RIC regimens span a number of days, including 2, 3, 4, 5, 6, 7, 8, 9, 10, 15, or 30 or more days. It is to be understood that in such instances, a subject may undergo an RIC regimen daily, or every 2, 3, 4, 5, or 6 days, for example. Additionally, the RIC regimens may be performed in a non-regular, or random, manner.

Additional Therapies

The repeated RIC regimen of the invention may be used in combination with other therapies or procedures aimed at treating traumatic injury, blood loss, hemorrhage, and/or shock. Depending upon the embodiment, one or more of these agents may be administered before, simultaneously with or following one or more RIC regimens and/or before, simultaneously with or following trauma. Trauma victims may be administered an anaesthetic simply to alleviate pain associated with the traumatic injury.

In some embodiments, the subject is administered a potassium channel opener or agonist. In some embodiments, the subject is administered an adenosine receptor agonist. In some embodiments, the subject is administered both of the foregoing agents.

Potassium channel openers include without limitation nicorandil, diazoxide, minoxidil, pinacidil, aprikalim, cromokulim and derivative U-89232, P-1075 (a selective plasma membrane K-ATP channel opener), emakalim, YM-934, (+)-7,8-dihydro-6,6-dimethyl-7-hydroxy-8-(2-oxo-1-piperidinyl)-6H-pyrano[-2,3-f]benz-2,1,3-oxadiazole (NIP-121), RO316930, RWJ29009, SDZPCO400, rimakalim, symakalim, YM099, 2-(7,8-dihydro-6,6-dimethyl-6H-[1,4]oxazino[2,3-f][2,1,3]benzoxadiazol-8-yl)pyridine N-oxide, 9-(3-cyanophenyl)-3,4,6,7,9,10-hexahydro-1,8-(2H,5H)-acridinedione (ZM244085), [(9R)-9-(4-fluoro-3-125iodophenyl)-2,3,5,9-tetrahydro-4H-pyrano[3,4-b]thieno[2,3-e]pyridin-8(7H)-one-1,1-dioxide] ([125I]A-312110), (−)-N-(2-ethoxyphenyl)-N'-(1,2,3-trimethylpropyl)-2-nitroethene-1,1-diami-ne (Bay X 9228), N-(4-benzoyl phenyl)-3,3,3-trifluoro-2-hydroxy-2-methyl-propionamine (ZD6169), ZD6169 (K-ATP opener) and ZD0947 (K-ATP opener), WAY-133537 and a novel dihydropyridine potassium channel opener, A-278637. In addition, potassium channel openers can be selected from BK-activators (also called BK-openers or BK(Ca)-type potassium channel openers or large-conductance calcium-activated potassium channel openers) such as benzimidazolone derivatives NS004 (5-trifluoromethyl-1-(5-chloro-2-hydroxyphenyl)-1,3-dihydro-2H-benzimidaz-ole-2-one), NS1619 (1,3-dihydro-1-[2-hydroxy-5-(trifluoromethyl)phenyl]-5-(trifluoromethyl)-2H-benzimidazol-2-one), NS1608 (N-(3-(trifluoromethyl)phenyl)-N'-(2-hydroxy-5-chlorophenyl) urea), BMS-204352, retigabine (also GABA agonist). There are also intermediate (eg. benzoxazoles, chlorzoxazone and zoxazolamine) and small-conductance calcium-activated potassium channel openers. Other compounds that are believed to open K-ATP channels include Levosimendan and hydrogen sulphide gas (H.sub.2S) or the H.sub.2S donors (eg sodium hydrosulphide, NaHS).

Adenosine receptor agonists include without limitation $N^6$-cyclopentyladenosine (CPA), N-ethylcarboxamido adenosine (NECA), 2-[p-(2-carboxyethyl)phenethyl-amino-5'-N-ethylcarboxamido adenosine (CGS-21680), 2-chloro-adenosine, $N^6$-[2-(3,5-demethoxyphenyl)-2-(2-methoxyphenyl]ethyladenosine, 2-chloro-N-6-cyclopentyladenosine (CCPA), N-(4-aminobenzyl)-9-[5-(methylcarbonyl)-beta-D-robofuranosyl]-adenine (AB-MECA), ([IS-[1a,2b,3b,4a(S*)]]-4-[7-[[2-(3-chloro-2-thienyl)-1-methyl-propyl]amino]-3H-imidazole[4,5-b] pyridyl-3-yl]cyclopentane carboxamide (AMP579), $N^6$-(R)-phenylisopropyladenosine (R-PLA), aminophenylethyladenosine (APNEA) and cyclohexyladenosine (CHA).

Adenosine A1 receptor agonists include without limitation N-[3-(R)-tetrahydrofuranyl]-6-aminopurine riboside (CVT-510), or partial agonists such as CVT-2759 and allosteric enhancers such as PD81723. Other agonists may include $N^6$-cyclopentyl-2-(3 phenylaminocarbonyltriazene-1-yl)adenosine (TCPA).

In some embodiments, the subjects may be administered anti-inflammatory agents, beta blockers (i.e., beta-adrenergic blocking agents) and/or calcium channel blockers.

Anti-inflammatory agents include without limitation Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium;

Triclonide; Triflumidate; Zidometacin; Glucocorticoids; Zomepirac Sodium. One preferred anti-inflammatory agent is aspirin.

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of five major chemical groups of drugs. These are the dihydropyridines, such as nifedipine, nicardipine, and nimodipine; the phenyl alkyl amines, such as verapamil; the benzothiazepines, such as diltiazem; the diarylaminopropylamine ethers, such as bepridil; and the benzimidazole-substituted tetralines, such as mibefradil.

Other calcium channel blockers useful according to the invention include but are not limited to aminone, amlodipine, bencyclane, felodipine, fendiline, flunarizine, isradipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

Beta-adrenergic receptor blocking agents are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitril HCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

In some embodiments, the subjects may be administered antioxidant agents.

Antioxidants are agents that reduce or prevent damage associated with oxidation in tissue or organs. Antioxidants include without limitation allopurinol, carnosine, histidine, Coenzyme Q 10, n-acetyl-cysteine, superoxide dismutase (SOD), glutathione reductase (GR), glutathione peroxidase (GP) modulators and regulators, catalase and the other metalloenzymes, NADPH and AND(P)H oxidase inhibitors, glutathione, U-74006F, vitamin E, Trolox (soluble form of vitamin E), other tocopherols (gamma and alpha, beta, delta), tocotrienols, ascorbic acid, Vitamin C, Beta-Carotene (plant form of vitamin A), selenium, Gamma Linoleic Acid (GLA), alpha-lipoic acid, uric acid (urate), curcumin, bilirubin, proanthocyanidins, epigallocatechin gallate, Lutein, lycopene, bioflavonoids, polyphenols, Trolox®, dimethylthiourea, Tempol®, carotenoids, coenzyme Q, melatonin, flavonoids, polyphenols, aminoindoles, probucol and nitecapone, 21-aminosteroids or lazaroids, sulphydryl-containing compounds (thiazolidine, Ebselen, dithiolethiones), and N-acetylcysteine.

Other antioxidants include the ACE inhibitors which are described in greater detail below. Other antioxidants include beta-mercaptopropionylglycine, O-phenanthroline, dithiocarbamate, selegilize, desferrioxamine (Desferal), 5'-5-dimethyl-1-pyrrolione-N-oxide (DMPO) and (a-4-pyridyl-1-oxide)-N-t-butylnitrone (POBN). Other antioxidants include nitrone radical scavenger alpha-phenyl-tert-N-butyl nitrone (PBN) and derivatives PBN (including disulphur derivatives); N-2-mercaptopropionyl glycine (MPG) a specific scavenger of the OH free radical; lipooxygenase inhibitor nordihydroguaretic acid (NDGA); Alpha Lipoic Acid; Chondroitin Sulfate; L-Cysteine; oxypurinol and Zinc.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [($San^1$)($Val^5$)($Ala^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclohexapentanoyl-N-hexylamide, Sankyo Company, Ltd., Tokyo, Japan); SKF108566 (E-alpha-2-[2-butyl-1-(carboxy phenyl)methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

ACE inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

In some embodiments, the subject is administered HMG-CoA reductase inhibitors. Examples include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860, U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

It is to be understood that the invention contemplates the use of one or more of any of the foregoing agents in combination with RIC of the invention.

RIC

As used herein, a RIC regimen is at least one cycle of an induced transient ischemic event followed by a reperfusion event. Typically, these regimens are performed by restricting blood flow in a limb or a peripheral tissue of the subject and then removing the blood flow restriction and allowing blood to reperfuse the limb or tissue. A regimen may comprise a single cycle or multiple cycles, including 2, 3, 4, 5, or more cycles. In one important embodiment, a regimen comprises 4 cycles of ischemia and reperfusion.

The blood flow restriction typically takes the form of an applied pressure to the limb or tissue that occludes blood flow. The applied pressure to the limb or tissue may be above systolic pressure (i.e., supra-systolic pressure). It may be about 5, about 10, about 15, about 20, or more mmHg above (or greater than) systolic pressure. Since systolic pressure will differ between subjects, the absolute pressure needed to induce ischemia will vary between subjects. In other embodiments, the pressure may be preset at, for example, 200 mmHg. In some embodiments, the applied pressure is less than systolic pressure provided blood flow is occluded. It is to be understood that, as used herein, blood flow occlusion refers to cessation of blood flow. As described herein, such blood flow occlusion or cessation occurs in a region of the body that is remote from a site of injury or one or more organs being protected from such injury. For example, blood flow occlusion or cessation may occur in a lower limb and/or an upper limb.

The blood flow restriction or occlusion may be accomplished using any method as the invention is not limited in this regard. Typically, it may be accomplished with an inflatable cuff, although a tourniquet system is also suitable. Further examples of automated devices for performing RIC are described below.

The induced ischemic event is transient. That is, it may have a duration of about 1, about 2, about 3, about 4, about 5, or more minutes. Similarly, the reperfusion event may have a duration of about 1, about 2, about 3, about 4, about 5, or more minutes.

If performed using a limb, the upper limb or lower limb may be used. In some instances the upper limb is preferred. In some instances the lower limb is preferred. In some instances, RIC is performed on two different sites on the body, in an overlapping or simultaneous manner.

RIC may be performed using any device provided it is capable of inducing transient ischemia and reperfusion, whether manually or automatically.

In one of its simplest forms, the method may be carried out using a sphygmomanometer (i.e., the instrument typically used to measure a subject's blood pressure). The cuff of the sphygmomanometer is placed about a subject's limb (e.g., an arm or leg) and is inflated to a pressure great enough to occlude blood flow through the limb (i.e., a pressure greater than the subject's systolic blood pressure). The cuff is maintained in the inflated state to prevent blood flow through the limb for a specified period of time, referred to herein as the ischemic duration. After the ischemic duration, pressure is released from the cuff to allow reperfusion of blood through the limb for a period of time that is referred herein as the reperfusion duration. The cuff is then re-inflated and the procedure is immediately repeated a number of times.

The method may similarly be carried out using a manual type tourniquet. Devices such as those described in published PCT application WO 83/00995 and in published US application 20060058717 may also be used.

Another system that may be used is described in published US application 20080139949. The advantage of this system is that it can be used independently of a medical practitioner, and that it automatically induces the required RIC regimen. This system is exemplified in part in FIG. 1, which illustrates a cuff 10, an actuator 12, a controller 14 and a user interface 16. The cuff is configured to be placed about the limb 15 of a subject, such as an arm or leg of the subject. The actuator, when actuated, causes the cuff to retract about the limb to occlude blood flow through the limb. The controller executes a protocol that comprises repeating a cycle one or more times. The cycle itself includes actuating the cuff to prevent blood flow, maintaining the cuff in an actuated state for an ischemic duration, releasing the cuff, and maintaining the cuff in a relaxed state to allow reperfusion.

Figure 2:
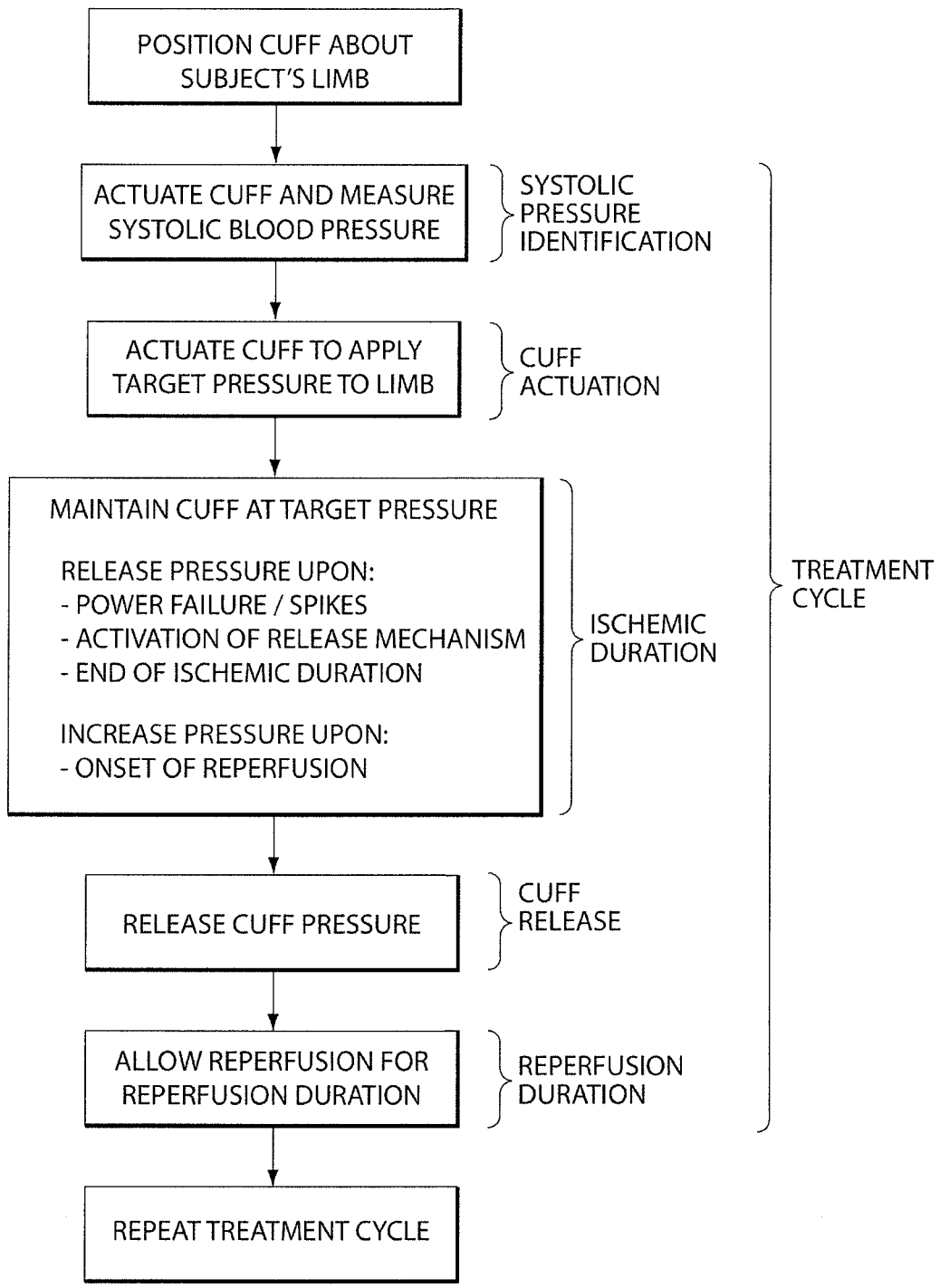
FIG. 2 is a block diagram of one embodiment of an operating scheme of the RIC system.

FIG. 2 shows a block diagram that represents a scheme that may be used to perform RIC. The scheme begins with placement of a cuff about a subject's limb. The system is then activated and the protocol is initiated through the controller. In one embodiment, the system is activated by a medical professional. In another embodiment, the system may be activated by the subject. The cuff contracts to apply an initial pressure, greater than systolic pressure, to the subject's limb. As discussed herein, the initial pressure may be a default value of the system or may be programmed into a particular protocol. The cuff then deflates to identify the subject's systolic pressure. This may be accompanied by monitoring the subject for the onset of Korotkoff sounds or vibrations. Alternatively or additionally, a distal remote sensor (e.g., a device on the fingertip which is sensitive to the presence or absence of flow or maintenance of flow) may be used. Once systolic pressure has been identified, the system initiates the first cycle of the protocol. In some embodiments, systolic pressure may be identified as an initial portion of the protocol. As used herein, the terms protocol and regimen are used interchangeably.

The cycle begins as the cuff contracts to apply a target pressure, greater than the subject's systolic pressure by an amount defined in the protocol, to the subject's limb. This occludes blood flow through the subject's limb. The external pressure against the subject's limb is held for an ischemic duration defined in the protocol. The system monitors the subject during the ischemic duration for pressure release criteria, which may include system power failure, system power spikes, and manual activation of quick release mechanism. The system also monitors the subject during the ischemic duration for any signs of reperfusion through the subject's limb, and accordingly, increases the external pressure applied by the cuff to prevent such reperfusion. Signs of reperfusion can include the onset of Korotkoff sounds or vibrations. After passage of the ischemic duration, the cuff releases pressure from about the subject's limb to allow reperfusion. Reperfusion is allowed for a reperfusion duration defined in the cycle.

The initial cycle typically concludes after the reperfusion duration. At this time, a subsequent cycle may begin as the cuff is actuated to contract about the subject's limb to occlude blood flow through the limb for another ischemic duration.

The cuff illustrated in FIG. 1 is configured to be positioned about the limb of a subject and to contract about the limb when actuated. In one embodiment, the sleeve is wrapped about a subject's upper arm, calf, or thigh and is fastened snuggly in place. Portions of the cuff may include hook and loop type material that can be used to fasten the sleeve in place about the subject's limb. The actuator inflates the cuff such that the limb is constricted to the point of occluding blood flow through the subject's limb.

The illustrated cuff includes an inflatable bladder (not shown) that receives a fluid, such as air, to cause the cuff expand and retract about a subject's limb. The bladder is constructed of an air impermeable material, such as flexible plastic or rubber. A connection port 18 is present at one end of the bladder to allow air to enter the bladder during inflation, or to exit the bladder during deflation. The port may include engagement features to facilitate a connection to the actuator, such as by an air hose. These features may include threads, clips, and the like. Although the illustrated embodiment includes a single bladder positioned within a cuff, it is to be appreciated that other embodiments are also possible. By way of example, according to some embodiments, the fabric sleeve may itself be air impermeable, such that no separate bladder is required. In other embodiments, multiple, separate inflatable bladders may be incorporated into a common sleeve, as aspects of the present invention are not limited in this respect.

The general size of subjects that undergo RIC may vary greatly, particularly given the range of species to which the methods may be applied. Given this variance, it may be desirable for some embodiments of cuffs to be adjustable over a wide range to accommodate the variety of subject limb girths that may be expected. According to some embodiments, the cuff comprises an inflatable fabric sleeve having a length greater than three feet, such that a girth of up to three feet may be accommodated. Embodiments of cuffs may include a width as small as two inches, one inch, or even smaller, so as to accommodate the upper arm or leg of a much smaller subject, including a neonatal infant. It is to be appreciated, however, that other embodiments may be configured to encircle a much smaller range of limb sizes, as aspects of the present invention are not limited in this regard.

Various devices may be used as an actuator to constrict the cuff about a subject's limb, or to release the cuff. As illustrated in embodiment of FIG. 1, the actuator includes a pneumatic pump to provide pressurized air to an inflatable cuff through an air hose. The actuator also includes a release valve 20 that, when actuated, opens a passageway between the inflatable cuff and the external environment to allow pressurized air to escape from the cuff, so that the cuff loosens about the subject's limb.

The air pump can comprise any device capable of delivering compressed air. According to some embodiments, the air pump includes a piston compressor, although other types of pumps, like centrifugal pumps and scroll compressor may also be used. The pump may be configured to provide air flow at a rate of between 0.1 to 20 cubic feet per minute, with a head pressure of up to 50 psi, according to some embodiments. However, other flow rates and/or pressures are possible, as aspects of the invention are not limited in this respect.

The device may therefore comprise or be suited for use with a compressed air canister or cartridge. Pressurized gas (e.g., air) can then be used to inflate the band, thereby constricting the limb. In certain situations, including situations in which traumatic injury is common or likely (e.g., on a battlefield), the use of compressed gas may be more suitable than other inflation or constriction mechanisms. As an example, compressed gas canisters or cartridges are less likely to become clogged or otherwise fouled by debris that may be encountered (e.g., such as mud, dirt, water, etc. that exists in battlefield environments).

As discussed above, the actuator may also include a release mechanism to release a cuff from about the subject's limb. In the illustrated embodiment, the release comprises a release valve 20 that is positioned within the controller housing. The release valve, as shown, may be a solenoid that moves rapidly between fully closed and fully open positions to rapidly release air from the cuff and, in turn, to rapidly release the cuff from a subject. According to some embodiments, the same release valve or another release valve may also be actuated to open slowly, such as to adjust the pressure of the cuff or to allow a more controlled release of pressure such as may be required when the subject's blood pressure is measured.

Embodiments of the system may include safety features to allow rapid release of the cuff from a subject's limb. Moreover, some of these embodiments may be readily activated by a subject, such as when the subject feels discomfort. In one embodiment, the safety release 22 includes a large button positioned on or near the cuff. In this regard, the safety release is within reach of the subject. In other embodiments, the safety release may comprise a separate actuator, such as one that may be held in the free hand of the subject. Activating the safety release may cause the release valve of a pneumatic cuff to open, thereby allowing rapid removal of air from the cuff.

The system may also include a continually operating, cuff release mechanism. By way of example, a slow release valve may be incorporated into a pneumatic cuff to provide for a continual, slow release of pressurized air from the cuff. The continual slow release mechanism may provide for the safe release of a subject's limb, even in the face of power failures or other events that may prevent redundant safety features from operating properly. Similar type mechanism may be incorporated into embodiments that do not utilize a pneumatically inflatable cuff, as continual slow release mechanisms are not limited to pneumatic cuffs.

Embodiments of the system include a controller that receives information from a protocol and any other sensors in the system to, in turn, control the actuator to perform RIC. The controller and protocol combination may be implemented in any of numerous ways. For example, in one embodiment the controller and protocol combination may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the functions discussed herein. The one or more controllers can be implemented in numerous ways, such as with dedicated hardware, or with general purpose hardware (e.g., one or more processors) that is programmed using microcode or software to perform the functions recited above. The one or more controllers may be included in one or more host computers, one or more storage systems, or any other type of computer that may include one or more storage devices coupled to the one or more controllers. In one embodiment, the controller includes a communication link to communicate wirelessly, or via electrical or optical cable, to a remote location.

In this respect, it should be appreciated that one implementation of the embodiments of the present invention comprises at least one computer-readable medium (e.g., a computer memory, a floppy disk, a compact disk, a tape, etc.) encoded with a protocol in the form of a computer program (i.e., a plurality of instructions), which, when executed by the controller, performs the herein-discussed functions of the embodiments of the present invention. The computer-readable medium can be transportable such that the protocol stored thereon can be loaded onto any computer system resource to implement the aspects of the present invention discussed herein. In addition, it should be appreciated that the reference to a protocol or controller which, when executed, performs the herein-discussed functions, is not limited to an application program running on a host computer. Rather, the term protocol is used herein in a generic sense to reference any type of computer code (e.g., software or microcode) that can be employed to program a processor to implement the herein-discussed aspects of the present invention.

The system may also comprise one or more sensors 26 that receive information from the subject and/or portions of the system itself. Such sensors may receive information regarding blood flow in any portion of the subject, including the limb that is being treated. These sensors may also receive information regarding other operating parameters of the system, such as air pressure within a pneumatic cuff, direct readings of pressure applied by cuff, or tension within portions of a tension band.

Pneumatic cuffs may include a sensor to measure pressure within the cuff. Cuff pressure is often directly indicative of the pressure that exists within a blood vessel of the limb beneath the cuff. The controller of a system is often programmed to target a particular cuff pressure that is to be maintained during the ischemic duration of a cycle, as is discussed herein. In embodiments that include a pneumatic cuff, the pressure sensor may be positioned anywhere within the pressurized space of the cuff, the air hose, or even within the actuator itself. Pressure sensors may also be positioned on an inner surface of the cuff to directly measure the pressure between the cuff and an outer surface of the subject's limb. In use, the cuff may be oriented such that the pressure sensor is positioned directly above the subject's artery, so as to provide a more direct measurement of pressure at a blood vessel of interest.

In one embodiment, systems may also include one or more vibration and/or ultrasonic sensors 28 to identify Korotkoff sounds. Korotkoff sounds are generally understood to be present when pressures between systolic and diastolic are externally applied to the artery of a subject. Systolic pressure is associated with a pressure value that completely occludes blood flow through a subject's blood vessels, and in this regard, may be used by the system as feedback to identify when pressure in the system is low enough to allow blood flow, or high enough to occlude blood flow.

One or more sensors may be included to confirm the cessation of blood flow or reperfusion in the limb that receives the cuff. For instance, in some embodiments, a pulse oximeter 30 may be positioned on a distal portion of the limb that receives the cuff, such as on a finger or toe of the limb. The pulse oximeter can provide information regarding blood pulsing through the subject's blood vessels and the percentage of haemoglobin that is saturated with oxygen. The pulse oximeter will detect an absence of pulses when blood flow though a limb is not occurring to confirm the occlusion of blood flow. Moreover, the pulse oximeter may also detect the percentage of haemoglobin saturated with oxygen, which will drop as blood flow through the limb ceases. It is to be appreciated that other sensors may also be used to confirm the cessation of blood flow, such as a photoplethysmographic transducer, an ultrasonic flow transducer, a temperature transducer, an infrared detector, and a near infrared transducer, as aspects of the invention are not limited in this respect.

As mentioned above, the system includes a protocol that, through the controller, directs the operation of the system. Embodiments of the protocol include a cycle that comprises cuff actuation, an ischemic duration, cuff release, and a reperfusion duration. In many embodiments of protocols, the cycle may be repeated multiple times. Additionally, some embodiments of the protocol include systolic pressure identification.

The cuff actuation portion of the cycle comprises contracting the cuff about the limb of a subject to occlude blood flow through the limb. Contraction of the cuff is accomplished by the controller reading instructions from the protocol, such as a target set point for cuff pressure, and then by the initiating the controller to bring the cuff to the target set point. Attainment of the target set point may be sensed through any of the herein described sensors and techniques.

During the ischemic phase of the cycle, pressure is maintained about the subject's limb to prevent reperfusion of blood flow through the limb. The length of the ischemic phase, termed the ischemic duration, is typically defined by a doctor, or other medical professional, and is programmed into the protocol. Ischemic duration may be as short as a few seconds, or as long as 20 minutes, or even longer, as aspects of the invention are not limited in this regard. In some embodiments, the ischemic duration varies from cycle to cycle during the same protocol, although in other embodiments, the ischemic duration remains constant.

The controller acts to maintain pressure, applied by the cuff, at a set point above the subject's systolic pressure. Embodiments of the cuff may relax relative to the subject's limb over time, thereby reducing pressure and eventually allowing reperfusion. This may be caused by various factors, including relaxation of muscles in the subject's limb, stretching of the cuff about the limb, air leaks (intentional or unintentional), and the like. To this end, a sensor may provide pressure readings as feedback to the controller. The controller can measure any difference between the set point and the actual pressure reading and can provide any necessary commands to the actuator to compensate for errors.

Various approaches may be used to define an appropriate set point for the controller during the ischemic duration. According to one embodiment, the set point is manually entered into the protocol by the doctor (or other medical professional). Alternately, the doctor may select a set point in terms of the subject's systolic blood pressure. In one embodiment, the set point may be selected as a fixed pressure amount over the subject's systolic blood pressure, such as 5 mmHg, 10 mmHg, 15 mmHg, 20 mmHg, 25 mmHg, 30 mmHg, or any other fixed amount above systolic pressure of the subject. In other embodiments, the set point may be defined as a percentage of the subject's systolic blood pressure, such as 102% of systolic, 105%, 110%, 115%, and other percentages, as aspects of the invention are not limited in this respect. The point above systolic pressure may be set by the medical professional and may be dependent upon several factors including, but not limited to the size of the subject, the size of the subject's limb, the subject's blood pressure, confirmation of blood flow cessation, and the like. In still other embodiments, the pressure may be set below systolic pressure, such as but not limited to 95%, 96%, 97%, 98%, or 99% of systolic pressure, provided that blood flow is occluded at such pressure, as may be achieved by varying cuff parameters.

The protocol, according to some embodiments, includes phases to identify the subject's systolic blood pressure. The cuff may be allowed to loosen about the subject's limb, from a point believed to be above systolic pressure, in a systematic manner while sensors are monitoring the limb for the onset of Korotkoff sounds or vibrations. Once the systolic pressure is identified, the protocol may continue in the normal course.

Identification of systolic pressure may optionally occur at any time during a protocol, or not at all. According to some embodiments, each cycle begins with the identification of the subject's systolic blood pressure. In other embodiments, systolic pressure may be identified only once during an initial portion of the protocol. In still other embodiments, systolic pressure may be identified as the cuff is released during the cuff release portion of each cycle. Still, as discuss herein, systolic pressure may not be identified at all during a protocol, as aspects of the invention are not limited in this regard.

The system can be configured to adjust the pressure set point during the ischemic duration. As discussed herein, the system may include sensors that detect the onset of reperfusion. As an example, this may be accomplished by detecting the presence of Korotkoff sounds or vibrations. The presence of Korotkoff sounds during an ischemic duration can indicate that either cuff pressure has fallen below systolic or that systolic pressure has risen above the set point that was previously above systolic pressure. Other devices may additionally or alternatively be used including for example devices on digits that detect the presence or absence of flow. In such a situation, the controller may adjust the set point based on the newly identified systolic pressure and/or other information and in this regard, can identify and prevent unwanted reperfusion that might otherwise occur.

The cuff release portion of a cycle occurs at the end of the ischemic duration and includes release of the cuff to a point below diastolic pressure. According to some embodiments, cuff release comprises releasing the pressure or tension of the cuff. In embodiments that utilize a pneumatic cuff, this may simply be associated with moving an air release valve to the fully open position to allow a rapid reduction in cuff pressure and a corresponding rapid relaxation of the cuff about the subject's limb. However, it is to be appreciated, that in other embodiments, that cuff relaxation may occur in a slower, more controlled manner, as aspects of the invention are not limited in this respect. Additionally, as discussed herein, the cuff release may be accompanied by monitoring for the onset of Korotkoff sounds or vibrations to identify or confirm the systolic pressure of the subject.

The reperfusion duration follows the cuff release in embodiments of the cycle. Reperfusion through the limb is allowed for a period of time termed the reperfusion duration. Much like the ischemic duration, reperfusion may be allowed for varied lengths of time, as short as a five seconds, one minute or more, and as long as 20 minutes, or even longer. The reperfusion duration may remain constant from cycle to cycle during a common protocol, or may vary between each cycle, as aspects of the invention are not limited in this respect.

The protocol may comprise any number of cycles. As discussed herein, a common cycle may simply be repeated a plurality of times, such as two, three, four, or more times, to complete a protocol. Alternately, the cycles of a protocol may be programmed with different parameters, such as different ischemic durations, reperfusion durations, pressure set points during the ischemic duration, and the like.

In some embodiments, the system may include a data logging feature that records the system parameters, such as cuff pressure or tension, during all phases of a protocol. Date of time of operation may also be recorded. Other features, such as personal information to identify the subject, may also be recorded by the system.

Embodiments of the system may incorporate various features to inform the subject or medical professional about the progress of the protocol. Audible or visual indicators may accompany any of the phases of the protocol. By way of example, a clock may show either the amount of time that has elapsed or that remains for a given portion of the protocol or the entire protocol. Embodiments may also include other features to keep the subject and/or medical professional informed, as aspects of the invention are not limited in this regard.

According to some embodiments, the system includes features to prevent tampering or accidental reprogramming by a subject. By way of example, in some embodiments, the reprogrammable features may only be accessed after entering a code. This can prevent a subject from mistakenly reprogramming the protocol or otherwise interfering with the operation of the system. It is to be appreciated that other devices may also be used to prevent accidental reprogramming, such as electronic keys, mechanical locks and the like.

The system may be configured for use is a variety of environments. By way of example, the system may be mounted on a portable stand with casters to facilitate easy movement. The stand may position the controller, user interface, and connections to the cuff at a convenient height for the subject. In other embodiments, the system is configured for portable use. In such embodiments, the system may be configured for ready placement into a suitcase for easy transport.

Figure 3:
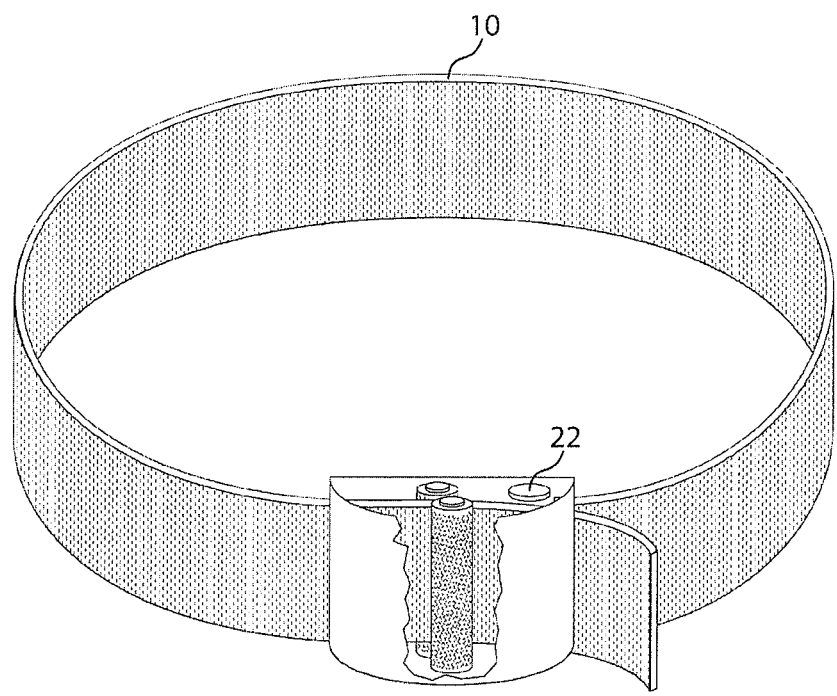
FIG. 3 shows an alternate embodiment of a cuff configured to contract about the limb of a subject.

The system is also not limited to components illustrated in the embodiment of FIG. 1. By way of example, according to other embodiments, like that illustrated in FIG. 3, cuffs may be configured to constrict a subject's limb through alternative mechanisms. In the illustrated embodiment, the cuff is configured as a band having a ratcheting mechanism positioned at one end. In use, the band is wrapped about the limb of a subject with the free end of the band passing through the ratcheting mechanism. In such an embodiment, the actuator may comprise a mechanism that pulls the free end of the band further through the ratcheting mechanism to retract the cuff about the limb, or that frees the ratcheting mechanism to release the band to, in turn, release the band from the limb. Still other mechanisms, such as tourniquet mechanisms, are possible, as aspects of the invention are not limited in this respect.

As described above with reference to FIG. 3, some embodiments may have a cuff that comprises a band that does not inflate, but rather is tightened about a subject's limb by another mechanism. In such embodiments, the actuator may comprise a tensioning mechanism configured to move one end of the band relative to other portions of the band so as to place the band in tension. As shown, the mechanism can include opposed rollers held in close proximity to one another within a housing. The housing includes a slot for receiving a free end of the band and a fixation point for fixed attachment to the opposite end of the band. The free end of the band is passed into the slot and between the rollers. The rollers may be mechanically actuated to rotate relative to one another, such as by an electric motor, to pull the free end through the housing and thus tighten the band around a subject's limb.

The tensioning mechanism may include opposed rollers mounted on a ratcheting, free wheel mechanism. The freewheel mechanism allows the band to be pulled through the slot in one direction with minimal resistance so that the band may be pulled rapidly to a snug position about a subject's limb. The free wheel mechanism also prevents the band from moving through the slot in the loosening direction, unless the mechanism is released or the opposed rollers are actuated. It is to be appreciated that not all embodiments will include a free wheel mechanism, as aspects of the invention are not limited in this regard.

The opposed rollers rotate in either direction to tighten and loosen the band during use. When required, the rollers may rapidly rotate until the band achieves a particular tension. The rollers may further be actuated to make minor adjustments to the tension in the band during use. When the cuff is to be released from the subject's limb, a ratcheting mechanism or clutch may be released such that the opposed rollers are allowed to move freely, thus rapidly releasing tension.

The invention contemplates the placement of a cuff or cuff-containing device such as those described herein within a garment, including but not limited to a military uniform. The cuff may be placed in a pant or leg portion or in the sleeve or arm portion of the garment. The garment may be designed such that the wearer is able to initiate one or more cycles of blood flow occlusion and reperfusion. The device may be capable of remote operation in the event that the wearer is unable to initiate the occlusion/reperfusion cycles.

Aspects of the invention are not limited to the embodiments of cuffs illustrated herein.

EXAMPLES

Resuscitated hemorrhagic shock following trauma is known to contribute to the development of late organ dysfunction in those who survive the initial trauma insult and thus contributes to morbidity and mortality in this patient population. A number of mechanisms have been implicated in this process, but the activation of proinflammatory signaling cascades leading to cellular death directly via apoptotic pathways or alternatively through priming of the innate immune cell system have been shown to be contributory. Strategies directed at preventing the onset of these pathways would clearly have potential benefit in reducing attendant morbidity and mortality related to organ injury.

Remote ischemic conditioning (RIC), a process whereby distant vascular beds are temporarily rendered ischemic, protects organs from the effects of ischemia/reperfusion (I/R) injury. For example, transient remote vascular occlusion has been shown to be protective of I/R injury in the heart, liver, lung, intestine and kidney. This Example shows the effect of RIC on end organ injury, particularly in the lung and liver, following hemorrhagic shock.

Materials and Methods:

Animal model of hemorrhagic shock (HS). Animals were cared for in accordance with the guidelines set forth by the Canadian Council on Animal Care. C57Bl/6 mice weighing 20 to 30 g (Charles River, St Constant, Quebec) were anaesthetized with intra-peritoneal ketamine (200 mg/kg) and xylazine (10 mg/kg). The right femoral artery was cannulated for hemorrhagic shock and resuscitation. Hemorrhagic shock was initiated by blood withdrawal equivalent to 20% of blood volume (22.5 mL of blood/kg) over 15 mins as previously reported. To prevent clotting, shed blood was collected in the presence of 3.8% Na-citrate. After a hypotensive period of 1-10 mins or 60 mins, animals were resuscitated by transfusion of the shed blood plus an equal volume of Ringer's Lactate using a timed-delivery pump system. Total resuscitation time was standardized to two hours. Sham animals were instrumented but not bled. Finally, animals were sacrificed at the end of the resuscitation period by pentobarbital overdose.

At the end of the resuscitation period (t=0) and at t=2, 4 and 6 h later, a tracheostomy was performed and alveolar cells were recovered by bronchoalveolar lavage (BAL). In some studies, cell count and differential were performed following Giemsa staining and in other studies lung were harvested for histopathology and determination of wet/dry ratios as a measure of lung injury. Cells recovered from BAL at the end of a resuscitation period have been reported to exhibit a primed phenotype (Rizoli et al. J Immunol 61(11):6288-6296, 1998). Cells recovered at t=0 following resuscitated HS were plated and then stimulated in vitro with LPS (100 ng/ml). Supernatants were recovered for measurement of TNF-α by ELISA. In some experiments, the pelleted cells were re-suspended in serum-free DMEM and processed for immunofluorescence staining or flow cytometry analysis. Primed cells have also been reported to exhibit augmented Toll-like receptor 4 on their plasma membrane as a measure of priming (Powers et al. J Exp Med 203(8):1951-1961, 2006).

Serum alanine aminotransferase (ALT) levels, an indicator of hepatocellular injury, were measured in blood samples obtained at different times after the end of the resuscitation period. Measurements of ALT were made using BIOTRON Diagnostic Kits. Liver tissue was fixed by immersion in formaldehyde, embedded by paraffin wax, and then cut in 5 μm slices. Sections were evaluated by light microscopy following staining by haematoxylin and eosin. TUNEL staining for apoptotic nuclei was detected in dewaxed sections using the DeadEnd Fluorometric TUNEL Kit (Promega Corp).

RIC Protocol. Animals were subjected to unilateral hindlimb ischemia (or sham operation) using an elastic band around the thigh for varying times and then released for an equivalent time prior to initiation of hemorrhagic shock. Animals were subjected to 10 min of ischemia followed by 10 min of reperfusion.

Statistical Analysis. The data are presented as mean±standard error of n determinations as indicated in the Figure legends. Data were analyzed by one-way analysis of variance, and Newman-Keuls Multiple Comparison Test post-hoc using the Prism software (GraphPad, San Diego, Calif.). Results were considered significant when p≤0.05. Significance is indicated with an asterisk.

Figure 4A:
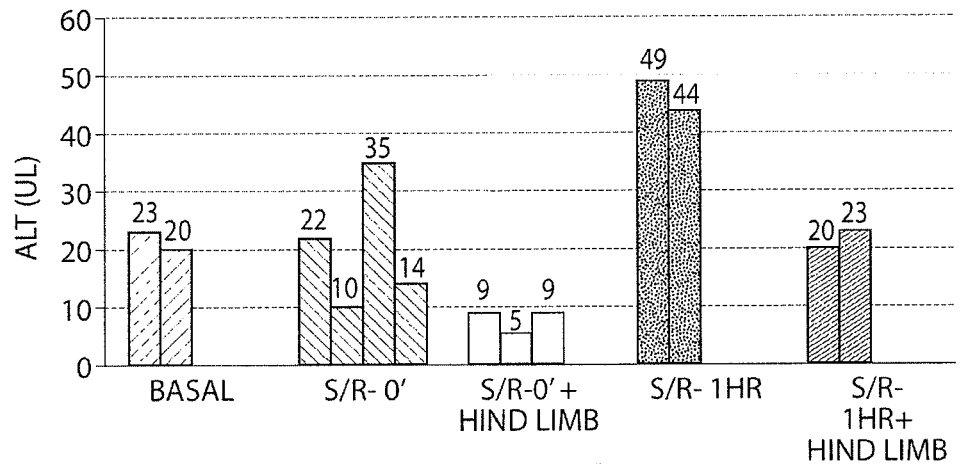
FIG. 4 shows the effect of RIC on shock and resuscitation induced liver damage in individual mice (A) and as an average (B).
Figure 4B:
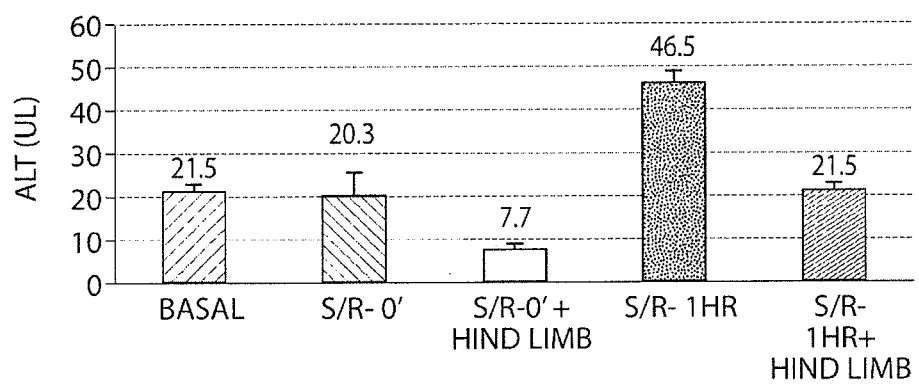

Results:

FIG. 4 shows the effect of RIC on shock-resuscitation induced liver damage as indicated by ALT levels in the treated subjects. FIG. 4A shows the results from individual subjects while FIG. 4B shows the results as the mean+/−standard error. The animals were divided into five groups as follows:

(i) basal, in which animals were treated as described above for sham;

(ii) S/R−0', in which animals were subjected to shock (15 mins of blood withdrawal) and then resuscitated within 0-10 minutes;

(iii) S/R−0'+Hind Limb, in which animals were ischemically conditioned prior to shock, then subjected to shock, and then resuscitated within 1-10 minutes;

(iv) S/R−1 HR, in which animals were subjected to shock and then resuscitated 60 minutes later; and (v) S/R−1 HR+Hind Limb, in which animals were ischemically conditioned prior to shock, then subjected to shock, and then resuscitated 60 minutes later.

FIG. 4 shows that, on average, RIC prevents liver damage, as measured by ALT levels, in subjects that have experienced hemorrhagic shock. RIC reduces and/or prevents liver damage in subjects that receive resuscitation therapy immediately following shock and in subjects that receive delayed resuscitation therapy.

Figure 5A:
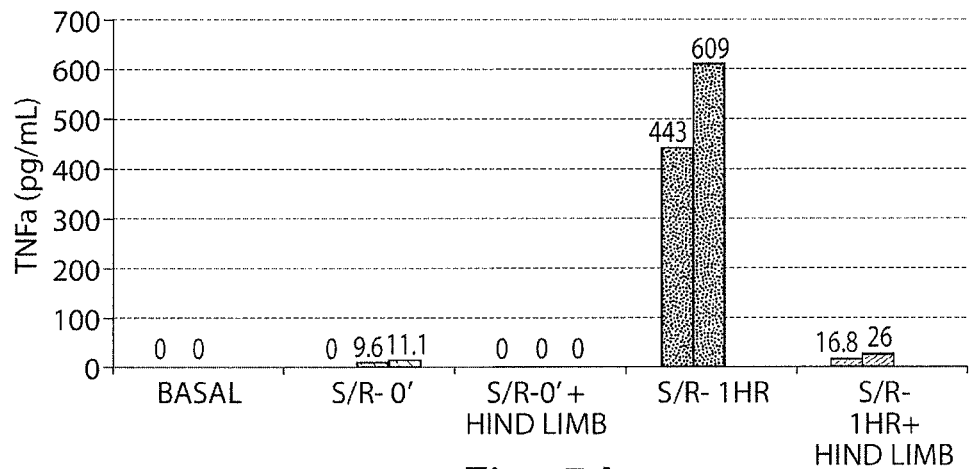
FIG. 5 shows the effect of RIC on shock and resuscitation induced serum TNF-alpha levels in individual mice (A) and as an average (B).
Figure 5B:
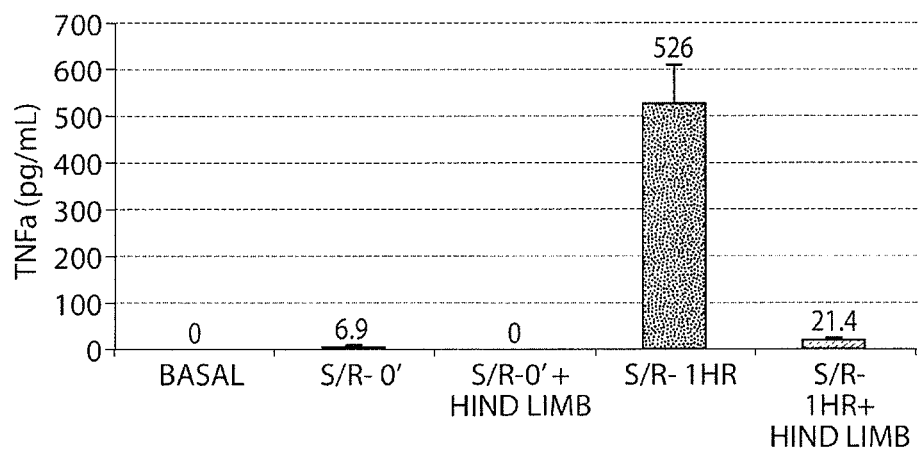

FIG. 5 shows the effect of RIC on shock-resuscitation induced TNF-alpha serum levels. TNF-alpha is a mediator of systemic inflammation and can be used as an indicator of liver damage. FIG. 5A shows the results from individual subjects while FIG. 5B shows the results as the mean+/−standard error. The animals were divided into five groups as described above for FIG. 4.

FIG. 5 shows that RIC prevents the induction of TNF-alpha levels following shock and resuscitation. In subjects that received RIC and were resuscitated within 0-10 minutes of shock, serum TNF-alpha was undetectable, as compared to an average level of 6.9 µg/ml in subjects that did not receive RIC. In subjects that received RIC and were resuscitated 60 minutes after shock, serum TNF-alpha level was reduced almost 25 fold, on average, as compared to subjects that did not receive RIC. The level of serum TNF-alpha in subjects receiving RIC and delayed resuscitation more closely resembled that of sham (untreated) subjects.

Accordingly, the data show that RIC reduces or prevents injury resulting from shock, whether the subjects receive immediate or delayed resuscitation therapy.

CONCLUSION

RIC represents a safe and effective approach to minimizing organ injury in subjects at risk for hemorrhagic shock. These findings have relevance to the preoperative surgical setting as well as civilian and military trauma injury.

The foregoing written specification is considered to be sufficient to enable one ordinarily skilled in the art to practice the invention. The present invention is not to be limited in scope by examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

What is claimed is:

1. A method for treating a subject experiencing, or likely to experience, hypovolemia caused by a traumatic injury to protect an organ of the subject from effects associated with hypovolemia, comprising:

performing non-invasive, individual or repeated remote ischemic conditioning (RIC) regimens on a subject experiencing or likely to experience hypovolemia caused by a traumatic injury, before performance of resuscitation therapy, wherein the RIC regimens are performed on a limb of the subject remote from the organ, wherein each RIC regimen comprises two or more cycles of blood flow occlusion followed by reperfusion, wherein each cycle of blood flow occlusion has duration of one minute or more and wherein each subsequent cycle begins upon conclusion of reperfusion of a previous cycle.

2. The method of claim 1, wherein repeated RIC regimens comprise more than one RIC regimen performed on a single day.

3. The method of claim 2, wherein repeated RIC regimens comprise two, three, four or five RIC regimens performed on a single day.

4. The method of claim 1, wherein repeated RIC regimens comprise one or more RIC regimens on more than one day.

5. The method of claim 1, wherein at least one RIC regimen is performed within 30 minutes or 1 hour of the traumatic injury.

6. The method of claim 1, wherein the RIC regimens are performed before the traumatic injury.

7. The method of claim 1, wherein the RIC regimens are performed before and after the traumatic injury.

8. The method of claim 1, wherein the RIC regimens are performed before, during and after the traumatic injury.

9. The method of claim 1, wherein the RIC regimens are performed during and after the traumatic injury.

10. The method of claim 1, wherein the RIC regimens are performed after the traumatic injury.

11. The method of claim 1, wherein the subject is human.

12. The method of claim 1, wherein at least one RIC regimen comprises at least four cycles, each cycle comprising occlusion and reperfusion.

13. The method of claim 1, wherein at least one RIC regimen comprises two or more cycles of 5 minutes of occlusion and 5 minutes of reperfusion.

14. The method of claim 1, wherein at least one RIC regimen comprises at least four cycles, each cycle comprising supra-systolic pressure and reperfusion.

15. The method of claim 14, wherein the supra-systolic pressure is a pressure that is at least 15 mmHg above systolic pressure.

16. The method of claim 14, wherein the supra-systolic pressure is a pressure that is about 200 mmHg.

17. The method of claim 1, wherein at least one RIC regimen comprises two or more cycles of 5 minutes of suprasystolic pressure and 5 minutes of reperfusion.

18. The method of claim 1, wherein repeated RIC regimens are performed at the same site.

19. The method of claim 1, wherein repeated RIC regimens are performed on an upper limb.

20. The method of claim 1, wherein repeated RIC regimens are performed on a lower limb.

21. The method of claim 1, wherein the subject is hypotensive.

22. A method for treating a subject for systemic effects associated with hypovolemia caused by a traumatic injury to protect one or more organs of the subject, comprising:

performing two or more cycles of non-invasive remote blood flow occlusion followed by reperfusion on a subject experiencing or likely to experience hypovolemia caused by a traumatic injury, before onset of ischemia and performance of resuscitation therapy, wherein the two or more cycles of non-invasive remote blood flow occlusion followed by reperfusion are performed on a limb of the subject remote from the one or more organs, wherein each cycle of blood flow occlusion has a duration of one minute or more and wherein each subsequent cycle begins upon conclusion of reperfusion of a previous cycle.

23. The method of claim 22, wherein the remote blood flow occlusion and reperfusion is performed on one or more lower and/or upper limbs.

24. A method for treating a subject who is experiencing or likely to experience hypovolemia and ischemia as a result of a traumatic injury to reduce or prevent systemic effects associated with hypovolemia to protect one or more organs, comprising performing individual or repeated remote ischemic conditioning (RIC) regimens on the subject before onset of ischemia and performance of resuscitation therapy, wherein the RIC regimens are performed on a limb of the subject remote from the one or more organs, wherein each RIC regimen comprises two or more cycles of blood flow occlusion followed by reperfusion, wherein each cycle of blood flow occlusion has a duration of one minute or more and wherein each subsequent cycle begins upon conclusion of reperfusion of a previous cycle.

* * * * *